United States Patent [19]

Eisenberg et al.

[11] Patent Number: 5,543,537

[45] Date of Patent: Aug. 6, 1996

[54] PROCESS FOR PREPARING TRIMETHYLALUMINUM

[75] Inventors: David C. Eisenberg; Milind M. Pradhan; Milham S. Howie, all of Baton Rouge, La.

[73] Assignee: Albemarle Corporation, Richmond, Va.

[21] Appl. No.: 436,695

[22] Filed: May 8, 1995

[51] Int. Cl.[6] ........................ C07F 5/06
[52] U.S. Cl. ............................ 556/157
[58] Field of Search ........................ 556/187

[56] References Cited

U.S. PATENT DOCUMENTS

| | | | |
|---|---|---|---|
| 4,118,409 | 10/1978 | Eidt et al. | 260/448 A |
| 4,364,872 | 12/1982 | Diefenbach | 260/448 A |
| 4,364,873 | 12/1982 | Diefenbach | 260/448 A |
| 4,364,874 | 12/1982 | Diefenbach | 260/448 A |
| 4,925,962 | 5/1990 | Beard et al. | 556/187 |
| 4,948,906 | 8/1990 | Beard | 556/187 |
| 5,015,750 | 5/1991 | Tran et al. | 556/187 |
| 5,359,116 | 10/1994 | Becker et al. | 556/187 |

*Primary Examiner*—Paul F. Shaver
*Attorney, Agent, or Firm*—David M. Bunnell

[57] ABSTRACT

Trimethylaluminum is made by an alkyl exchange process by first reacting a trialkylaluminum which has at least two carbon atoms in its alkyl groups with a methyl halide, optionally in the presence of an alkyl exchange catalyst, and then fractionally distilling trimethylaluminum from the product mixture in the presence of trialkylaluminum having at least two carbon atoms in its alkyl groups so as to convert the dimethylaluminum halide by-product of the alkyl exchange reaction into trimethylaluminum.

19 Claims, No Drawings

PROCESS FOR PREPARING TRIMETHYLALUMINUM

The invention relates generally to the preparation of trimethylaluminum and more particularly to an improved process for making trimethylaluminum by reacting a trialkylaluminum with a methyl halide, optionally in the presence of an alkyl exchange catalyst such as a bismuth catalyst, and then fractionally distilling the product in the presence of trialkylaluminum.

Trimethylaluminum is a useful component in forming polymerization catalyst compositions. One known process for forming trimethylaluminum involves the reaction of methyl-halides with trialkylaluminum compounds having at least two carbon atoms in its alkyl groups, such as triethylaluminum. The methyl groups exchange for the higher alkyl groups on the aluminum. For example, in U.S. Pat. No. 4,364,872, triethylaluminum is reacted with a methyl halide in the presence of a catalyst formed from a bismuth compound, such as $BiCl_3$, in an autoclave. In U.S. Pat. No. 4,364,873 a vanadium based catalyst is used to catalyze the exchange. In U.S. Pat. No. 4,364,874 an uncatalyzed exchange using an alkyl iodide is disclosed. More recently, U.S. Pat. No. 4,925,962 describes an improvement in which the methyl halide is gradually fed to the reaction and the alkyl halide co-product of the reaction, along with any unreacted methyl halide, are continuously distilled from the reaction mixture. The purpose of the removal is to avoid the accumulation of these materials in the reaction mixture. This reduces both the formation of dimethylaluminum halide by-product and the possibility of a thermal excursion in a large scale between the reactants due to high ratios of alkyl halide to alkylaluminum compound; the pressure generated could lead to a reactor rupture. Besides dimethylaluminum halide, $Me_3Bi$ is also formed in the reaction. The $Me_3Bi$ has about the same volatility as trimethylaluminum and, therefore, will distill over with the product as an impurity. Commercially available triethylaluminum, which is the preferred trialkylaluminum starting material, also contains some butyl groups which form butyl halide in the exchange reaction. Butyl halide in combination with trimethylaluminum can decompose in the fractionation column during the trimethylaluminum distillation and create a safety hazard.

We have now developed an improved process which not only reduces catalyst and butyl halide impurities in the trimethylaluminum product, but permits easy catalyst recycle and also converts dimethylaluminum halide by-product into trimethylaluminum and a less volatile dialkylaluminum halide which remains in the bottoms when the trimethylaluminum is distilled. Thus safety, trimethylaluminum yield, and trimethylaluminum quality are improved.

In accordance with this invention there is provided a process for making trimethylaluminum, said process comprising the steps of (a) reacting a trialkylaluminum having at least two carbon atoms in its alkyl groups with a methyl halide under reaction conditions so as to form a product mixture which contains trimethylaluminum and dimethylaluminum halide and (b) fractionally distilling trimethylaluminum from the product mixture in the presence of trialkylaluminum having at least two carbon atoms in its alkyl groups so as to convert at least a portion of the dimethylaluminum halide to trimethylaluminum. The trialkylaluminum for step (b) can be either added to the distillation and/or can be left over from the initial reaction in step (a) by, for example, adjusting the amount of methyl halide reactant so that not all of the triethylaluminum is consumed in the reaction. In another aspect of the invention, the product mixture is heated, preferably with aluminum powder, so as to precipitate bismuth catalyst from the product mixture and reduce the butyl bromide concentration. The recovered bismuth is an active catalyst and can be recycled.

The basic process to which the present process represents an improvement is described in detail in Diefenbach U.S. Pat. Nos. 4,364,872, 4,364,873 and 4,364,874 and Beard U.S. Pat. Nos. 4,948,906 and 4,925,962 which are incorporated herein in their entirety as if fully set forth.

Non-limiting examples of trialkylaluminum compounds in which the alkyl group contains at least two carbon atoms include triethylaluminum, tri-n-propylaluminum, tri-n-butylaluminum, tri-isobutylaluminum, tri-n-pentylaluminum, trihexylaluminum, and trioctylaluminum. By far the most preferred tri-$C_{2+}$ alkylaluminum compound is triethylaluminum because it is readily available at reasonable cost and its ethyl bromide co-product is easily removed from the reaction mixture. Mixtures of the trialkylaluminum containing up to about 60 wt. % of a dialkylaluminum halide having two or more carbons in its alkyl groups can also be used such as, for example mixtures of triethyl aluminum with diethylaluminum bromide.

Useful methyl halides include methyl chloride, methyl bromide and methyl iodide; the most preferred is methyl bromide. Methyl iodide is useful for the non-catalyzed reaction.

Non-limiting examples of alkyl exchange catalysts include the bismuth and vanadium based catalysts described in U.S. Pat. Nos. 4,364,872 and 4,364,873. Preferred are bismuth catalysts. Bismuth powder or any bismuth compound can be used to prepare the bismuth catalysts. It is believed that the bismuth reacts with the trialkylaluminum to form a compound which contains bismuth, aluminum and alkyl groups and possibly other groups. It is not necessary to know the structure of the active catalyst species in order to obtain the benefits of the reaction.

Preferred bismuth compounds are bismuth halides, bismuth oxides, and organobismuth compounds. Examples are bismuth trichloride, bismuth triiodide, bismuth tribromide, bismuth trifluoride, bismuth trioxide, triphenylbismuth, pentaphenylbismuth, trimethylbismuth, diphenylbismuth chloride, triethylbismuth, triphenylbismuth dichloride, bismuth triethoxide, bismuth triacetate, diethylbismuth bromide and the like.

Any trialkylaluminum can be used to form the catalyst, including trimethylaluminum. In a most preferred embodiment, bismuth powder is reacted with triethylaluminum and methyl bromide to form the catalyst. Bismuth powder is most preferred due to its low cost.

The amount of bismuth powder or bismuth compound used in the process can vary over a wide range. A useful range is about 0.5 to 10 mole percent based on the total amount of tri-$C_{2+}$ alkylaluminum used in the reaction. A preferred range is about 1 to 5 mole percent.

The process can be conducted in a solvent although this is not essential. Useful solvents include the inert liquid aliphatic hydrocarbons such as hexane, octane, decane, cyclohexane, cyclooctane. Aromatics such as benzene, toluene, xylene and the like can be used although this may lead to some nuclear alkylation.

Useful reaction temperatures are those that cause the exchange reaction to proceed at a reasonable rate but not so high as to cause the reactants or products to undergo undesired decomposition. A preferred temperature range is about 50°–150° C. A more preferred temperature range is about 115°–130° C. Temperatures above 127° C. will require some pressure in the reactor or the use of a reflux condenser so that the trimethylaluminum does not distill overhead.

In one mode of operation, the process can be carried out by placing all of the tri-$C_{2+}$ alkylaluminum reactant and the bismuth compound in a reaction vessel under an inert atmosphere, such as nitrogen. The mixture is stirred and heated to reaction temperature and then the methyl halide is introduced into the liquid phase at a controlled rate such that an excessive amount of methyl halide does not collect in the reactor. Most of the methyl halide will react with the tri-$C_{2+}$ alkyl aluminum under these conditions to form $C_{2+}$ alkyl halide and methylaluminum compounds. The reaction temperature must be high enough such that this $C_{2+}$ alkyl halide will vaporize from the reaction mixture. For example ethyl bromide has a normal boiling point of 38.4° C.

The reaction is conducted at atmospheric pressure or close to atmospheric pressure so the lower $C_{2+}$ alkyl halide will readily vaporize. About 10 to 25 percent, depending upon the feed rate and catalyst concentration, of the methyl halide will also escape the liquid reaction phase and be conducted from the reaction vessel together with the $C_{2+}$ alkyl halide. Some of the trimethylaluminum may also leave the reaction phase as a vapor and be separated by fractional distillation. In practice, about 2.5 to 4.0 moles of methyl halide will be injected into the liquid reaction phase per mole of tri-$C_{2+}$ alkylaluminum under reaction conditions so that about 10 to 20 mol percent of the tri-$C_{2+}$ alkylaluminum remains unreacted. The vented methyl halide, $C_{2+}$ alkyl halide, and TMA (if it is desired to remove some of the TMA continuously) can be condensed and separated by conventional means.

Progress of the reaction can be monitored by periodically withdrawing small samples from the reaction mixture and analyzing them.

After the desired amount of reaction has occurred, aluminum powder is added to the reaction mixture with heating at a temperature of from about 150° to 210° C. under pressure; this precipitates bismuth from the mixture. (Alkali and alkaline earth metals such as Na, K or Mg can also be used, but aluminum is preferred.) This process not only removes a potential source of bismuth impurity in the trimethylaluminum product, but the bismuth precipitate is an active catalyst which can be recycled to the exchange reaction. Amounts of aluminum or alkali or alkaline earth metals of from about 0.5 to 5.0 weight percent of the product mixture are preferred.

The aluminum treatment also has the beneficial effect of reducing the amount of butyl halide, such as BuBr, impurity which results from the normal presence of some butyl groups in the preferred starting material, triethylaluminum. The treatment also reduces the amount of any other halides present in the product mixture. Heating the reaction mixture without the aluminum will precipitate some, but not all, of the bismuth. After the bismuth has been precipitated, the product mixture is fractionally distilled to recover the trimethylaluminum product at temperatures of from about 50° to 90° C. and pressures of from about 50 to 200 mm Hg. During the distillation, the remaining triethylaluminum reacts with the by-product dimethylaluminum halide to form trimethylaluminum product, which distills off and diethylaluminum halide, which remains in the still bottoms. This exchange reaction is known, and is described, for example, in U.S. Pat. No. 4,118,409. If insufficient triethylaluminum remains in the product mixture from the original alkyl exchange reaction, then additional triethylaluminum can be added to the distillation. After the trimethylaluminum product has been recovered, the diethylaluminum halide bottoms can be easily decanted away from the precipitated bismuth catalyst, or partly recycled as a suspending medium for catalyst transfer. The bismuth catalyst can then be recycled to the initial alkyl exchange reactor without need for activation. A small amount of additional bismuth catalyst (about 10 to 20 percent of the original charge) can be added to make up for any losses in the decant.

The invention is further illustrated by, but is not intended to be limited to, the following examples.

EXAMPLE 1

Triethylaluminum (TEA) (70 grams) and $BiBr_3$ (3 grams, 1.1 mol percent Bi on aluminum) were placed in a dry, nitrogen purged 300 ml autoclave fitted with a 4-bladed impeller, cooling coil, thermocouple, MeBr addition tube, vent valve, and pressure transducer. The reactor was heated to 125° C. and MeBr was added with stirring, at a rate of 1.2 grams/min. until 125 grams had been added, and then at the rate of 0.9 grams/min. until a total of 173 grams had been added (MeBr/TEA mole ratio of 3.0). The reaction temperature was maintained at about 125° C. The EtBr co-product and any unreacted MeBr were vented through a valve which was used to control the back pressure at 3–6 psig. The vent gases were condensed by a dry ice condenser into a cooled heptane bath which was sampled and assayed for MeBr conversion by GC. The mole ratio by GC of EtBr to MeBr in the condensate flask was about 4:1. The mole ratio by NMR of $Me_3Al/Me_2AlBr$ in the reactor contents was about 2:1. The reactor contents were heated to 175° C. for 1 hour and some of the catalyst precipitated as Bi powder. The solution still contained about 0.3 wt. percent Bi. The reactor contents were co-distilled with 1.5 grams of TEA using a 7 in. column packed with glass helices. The contents of the distillation fractions in mmoles of each component are shown in Table 1.

TABLE 1

| | Codistillation of TEA with $Me_3Al/Me_2AlBr^a$ | | | | |
|---|---|---|---|---|---|
| Component | Initial Product Mixture + 1.5 g TEA 40 g total | 1st Fract 9.2 g | 2nd Fract 8.6 g | 3rd Fract 9 g | Bottoms 12.5 g |
| Br | 3.8 mmol/g | 0.1 mmol/g | 2.1 mmol/g | 4.9 mmol/g | 5.9 mmol/g |
| Al | 8.4 mmol/g | 11.4 mmol/g | 10 mmol/g | 7.2 mmol/g | 6.5 mmol/g |
| Me | 21.1 mmol/g | 39.9 mmol/g | 34.3 mmol/g | 18.1 mmol/g | 2.8 mmol/g |
| Et | 2.8 mmol/g | 0.04 mmol/g | 0.06 mmol/g | 0.24 mmol/g | 8.5 mmol/g |
| Bu | 0.3 mmol/g | | | | 0.67 mmol/g |

$^a$Reflux ratio = 4:1, 150–100 mm pressure

EXAMPLE 2

The process of Example 1 was repeated but using 100 grams of TEA and 5 grams of $BiBr_3$ (1.3 mole percent on Al) with 150 grams of MeBr initially added at the rate of 2.3 grams/min. and then 95 grams were added at a rate of 1.5 grams/min. for a total of 245 grams (mole ratio MeBr/TEA= 2.9). The EtBr/MeBr mole ratio of the condensate was about 3:1 and the $Me_3Al/Me_2AlBr$ mole ratio in the reactor was about 2:1. Some of bismuth catalyst was precipitated by heating the reaction mixture to 175° C. for 1 h.

EXAMPLE 3

The Bi precipitate from Example 2 was separated by decantation of the liquid phase and placed in an autoclave with 83 grams of TEA. MeBr was added to the autoclave, which was at a temperature of about 125° C. at the rate of 1.3 grams/min. until 125 grams had been added (MeBr/TEA=1.8). The recovered Bi catalyzed the exchange reaction with no loss of activity to produce trimethylaluminum and dimethylaluminum bromide at a 1:1 ratio and EtBr/MeBr in a 3:1 ratio. Adding 0.5 grams of aluminum powder (mole ratio Al/Bi≈2) and heating the product mixture at 175° C. for 1 hour precipitated all of the bismuth as a powder (<30 ppm Bi, detection limit). The amount of BuBr in the product mixture was also reduced.

EXAMPLE 4

The process of Example 1 was repeated using 100 grams of TEA and 2 grams of powdered bismuth (1.1 mol percent Bi on Al). MeBr was added at a rate of 1.0 gram/min. until 70 grams had been added and at a rate of 1.5 grams/min. until a total of 315 grams had been added (MeBr/TEA=3.8). The reaction temperature was 125° C. The mole ratio of $Me_3/Al$ to $Me_2AlBr$ was about 3:1 and that of EtBr to MeBr was about 3:2. The bismuth catalyst was precipitated by heat treatment with 1 g of Al powder at 170° C. for 1 hour. The product mixture was fractionally codistilled with 2.5 grams of added TEA. The results are shown in Table 2.

TABLE 2

| | Codistillation of TEA with $Me_3Al/Me_2AlBr^a$ | | | | |
|---|---|---|---|---|---|
| Component | Initial Product Mixture + 2.5 g TEA 43.5 g total | 1st Fract 3.0 g | 2nd Fract 8.2 g | 3rd Fract 10.6 g | Bottoms 18.4 g |
| Br | 3.0 mmol/g | 0.1 mmol/g | 0.2 mmol/g | 3.5 mmol/g | 4.7 mmol/g |
| Al | 9.7 mmol/g | 12.9 mmol/g | 13.2 mmol/g | 10.2 mmol/g | 7.3 mmol/g |
| Me | 18.6 mmol/g | 37.8 mmol/g | 37.0 mmol/g | 25.3 mmol/g | 2.6 mmol/g |
| Et | 4.2 mmol/g | 0.04 mmol/g | 0.04 mmol/g | 0.5 mmol/g | 8.6 mmol/g |
| Bu | 0.2 mmol/g | | | | 0.3 mmol/g |

$^a$Reflux ratio = 4:1; 150–100 mm Hg pressure

From the above examples it appears that a preferred mode of operation for the overall process is: About 1.5 mole percent of Bi powder (per mole of TEA) is used as the initial catalyst. MeBr is fed in against a back pressure of 3 to 15 psig while running the reaction at 120°–130° C. Initial activation of the bismuth powder requires a very slow feed (2–3 hours) for the first 15 percent of the MeBr or an induction period. The remaining feed time is 1.5 to 2.5 hours. MeBr addition is stopped when about 15 mol percent of the ethyl groups are still unreacted. Al powder (1 to 3 weight percent of initial TEA loading) is added and the reaction mixture is heated to 175° C. for 1 hour. TMA is distilled overhead using a 15–20 plate column at 100 mm Hg (any BuBr or light hydrocarbons remaining will come overhead first and be discarded). The $Et_2AlBr$ bottoms are decanted away from the precipitated Bi catalyst to the extent desired. A small amount of Bi powder is added (10 to 20 percent of original loading) to make up for Bi lost in the decant, and the process is repeated without the initial activation period.

What is claimed is:

1. A process for making trimethylaluminum, said process comprising the steps of (a) reacting a trialkylaluminum having at least two carbon atoms in its alkyl groups with a methyl halide under conditions to form a product mixture which contains trimethylaluminum and dimethylaluminum halide, and (b) fractionally distilling trimethylaluminum from said product mixture in the presence of trialkylaluminum having at least two carbon atoms in its alkyl groups so as to convert at least a portion of the dimethylaluminum halide to trimethylaluminum.

2. The process of claim 1 wherein an alkyl exchange catalyst is used in step (a).

3. The process of claim 2 wherein the catalyst is a bismuth catalyst.

4. The process of claim 3 wherein the product mixture from step (a) is heated with aluminum powder or an alkali or alkaline earth metal so as to precipitate the bismuth catalyst from the product mixture.

5. The process of claim 4 wherein the aluminum powder treatment also reduces the concentration of butyl halide in the product mixture.

6. The process of claim 1 wherein the trialkylaluminum is triethylaluminum and the methyl halide is methyl bromide.

7. The process of claim 3 wherein the trialkylaluminum is triethylaluminum and the methyl halide is methyl bromide.

8. The process of claim 3 wherein the catalyst is bismuth powder.

9. The process of claim 3 wherein the catalyst is a bismuth halide.

10. The process of claim 3 wherein the catalyst is bismuth oxide.

11. The process of claim 3 wherein the catalyst is triphenyl bismuth.

12. The process of claim 1 wherein a mixture of said trialkylaluminum and up to about 60 wt. % dialkylaluminum halide having at least two carbon atoms in its alkyl groups is reacted in step (a).

13. A process for making trimethylaluminum, said process comprising the steps of (a) reacting trialkylaluminum having at least two carbon atoms in its alkyl groups with a methyl halide under an inert atmosphere in the presence of a bismuth catalyst by feeding a methyl halide to a mixture of said trialkylaluminum and catalyst so as to form a product mixture comprising a $C_2$ or higher alkyl halide, trimethylaluminum and dimethylaluminum halide by-product while distilling said $C_2$ or higher alkyl halide and any unreacted methyl halide from said reaction, (b) discontinuing the feeding of said methyl halide when a portion of said trialkylaluminum still remains in the product mixture, (c) heating said product mixture so as to precipitate the bismuth catalyst from the product mixture, and (d) fractionally distilling trimethylaluminum from said product mixture while causing the remaining trialkylaluminum to react with the dimethylaluminum halide by-product during said distillation so as to form additional trimethylaluminum and a less volatile dialkylaluminum halide.

14. The process of claim 13 wherein aluminum powder is added to step (c).

15. The process of claim 13 wherein additional trialkylaluminum is added to step (d).

16. The process of claim 14 wherein about 10 to 25 mole percent of the trialkylaluminum remains unreacted when the methyl halide feed is discontinued.

17. The process of claim 13 wherein the trimethylaluminum is triethylaluminum and the methyl halide is methyl bromide.

18. The process of claim 13 wherein a portion of the trimethylaluminum is removed continuously during the step (a) reaction and separated by fractional distillation.

19. The process of claim 13 wherein a mixture of said trialkylaluminum and up to about 60 wt. % dialkylaluminum halide having at least two carbon atoms in its alkyl groups is reacted in step (a).

* * * * *